| United States Patent [19] | [11] | 4,328,153 |
|---|---|---|
| Brenner | [45] | May 4, 1982 |

[54] DOPAMINERGIC BENZAZEPINES

[75] Inventor: L. Martin Brenner, Havertown, Pa.

[73] Assignee: Smith Kline Corporation, Philadelphia, Pa.

[21] Appl. No.: 169,696

[22] Filed: Jul. 17, 1980

[51] Int. Cl.$^3$ .................... C07D 223/16; A61K 31/55
[52] U.S. Cl. ............................... 260/239 BB; 424/244
[58] Field of Search .................. 260/239 BB; 424/244

[56] References Cited

U.S. PATENT DOCUMENTS 3,609,138  9/1971  Mull et al. ..................... 260/239 BB
4,011,319  3/1977  Kaiser et al. ......................... 424/244
4,197,297  4/1980  Weinstock .................... 260/239 BB

FOREIGN PATENT DOCUMENTS 555831  11/1974  Switzerland .................. 260/239 BB

*Primary Examiner*—Glennon H. Hollrah
*Assistant Examiner*—D. B. Springer
*Attorney, Agent, or Firm*—William H. Edgerton; Richard D. Foggio; Alan D. Lourie

[57] ABSTRACT

A new series of compounds having renal vasodilating activity is described. The compounds are 3-cycloalkyl-methyl-7,8-dihydroxy-6-halo-1-(p-hydroxyphenyl)-2,3,4,5-tetrahydro-1H-3-benzazepines.

4 Claims, No Drawings

NEW DOPAMINERGIC BENZAZEPINES

This invention comprises a group of new chemical compounds which are 3-cycloalkylmethyl-7,8-dihydroxy-6-halo-1-(p-hydroxyphenyl)-2,3,4,5-tetrahydro-1H-3-benzazepines. These compounds increase blood flow in the kidney by decreasing vascular resistance mainly by means of a dopaminergic effect on peripheral dopamine receptors. As such they are useful for treating hypertension.

DESCRIPTION OF THE PRIOR ART

A number of 1-phenyl-2,3,4,5-tetrahydro-1H-3-benzazepines have been described which have renal dopaminergic activity such as U.S. Pat. Nos. 4,160,765; 4,197,297 and 4,251,525. These prior art compounds do not have the combination of structural features present in the compounds of this invention especially the 3-cycloalkylmethyl substituent. A number of other patents such as U.S. Pat. No. 3,609,138 or U.K. Pat. No. 1,268,243 disclose cycloalkylalkyl substituents at the 3-position of 2,3,4,5-tetrahydro-1H-3-benzazepines but for compounds having activity in a different therapeutic indication and with broad generic disclosures.

DESCRIPTION OF THE INVENTION

The compounds of this invention have structures characterized by a 2,3,4,5-tetrahydro-1H-3-benzazepine nucleus substituted by a cycloalkylmethyl group at position 3, a halo at position 6, two hydroxy groups at positions 7 and 8 and a hydroxyphenyl moiety at position 4. The compounds therefore may be represented by the following structural formula:

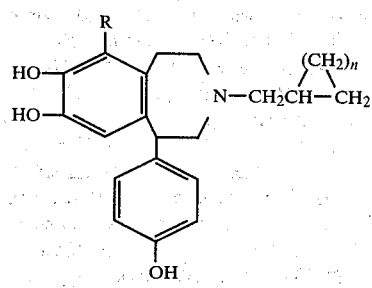

in which R is halo, that is, chloro, bromo, fluoro or iodo and n is an integer of from 1-4. Of particular interest are those compounds of Structure I in which n is 1.

The three phenolic hydroxy groups may also be derivatized by forming tri-lower alkanoyl esters. Each of the lower alkanoyl groups has from 2-7 carbon atoms. For convenience in preparation, the same alkanoyl group is used at each position.

The pharmaceutically acceptable acid addition salts having the utility of the free bases of Formula I, prepared by methods well known to the art, are formed with both inorganic and organic acids, for example: fumaric, ascorbic, succinic, methane sulfonic, ethanedisulfonic, acetic, tartaric, salicylic, citric, gluconic, itaconic, glycolic, benzene sulfonic, hydrochloric, hydrobromic, sulfuric, cyclohexylsulfamic, phosphoric and nitric acids. The hydrohalic and especially methane sulfonic acid salts are of particular utility.

The compounds of this invention are prepared by a synthetic sequence the first step of which involves the N-acylation of a known 6-halo-7,8-dimethoxy-1-(p-methoxyphenyl)-2,3,4,5-tetrahydro-1H-3-benzazepine (U.S. Pat. No. 4,160,765) with a cycloalkyl carboxylic acid or its acid halide to give the N-cycloalkylcarbonyl compound which is then reduced with metallic reducing agent such as lithium aluminum hydride, sodium borohydride, sodium cyanoborohydride, lithium triethylborohydride, sodium trimethoxyborohydrate and other metallic hydride reducing agents.

The reducing step is conveniently carried out in a solvent in which the reactants are soluble such as tetrahydrofuran at temperatures from 40° up to reflux temperature. The desired products are isolated by methods known to the art.

Most conveniently the acylation-reduction steps can be combined using a cycloalkylcarboxylic acid and the secondary base as starting material with sodium borohydride in tetrahydrofuran at 50°-60° until the reaction is complete.

Of particular interest is the final step of the reaction sequence in which the 3-cycloalkylmethyl-6-halo-7,8-dimethoxy-1-(p-methoxyphenyl)-2,3,4,5-tetrahydro-1H-3-benzazepine or one of its acid addition salts is reacted with an ether cleaving agent. Thr reaction readily proceeds with boron tribromide or boron trichloride in a halogenated organic solvent such as methylene chloride, carbon tetrachloride or chloroform. Alternative ether cleaving agents are pyridine hydrochloride, 48% aqueous hydrogen bromide, aluminum chloride or bromide in a suitable organic solvent such as benzene or carbon disulfide, 57% hydrogen iodide, hydrogen fluoride-antimony pentafluoride or trifluoromethylsulfonic acid in thioanisole. The product is isolated by methods known to the art.

Details of this reaction sequence are described in the exemplary material presented below. Other variations of the reaction sequence or indeed other synthetic paths to the final products will be apparent to those skilled in the art. Other O-protecting groups are useful such as benzyl, other lower alkyl groups for example ethyl, propyl, or for 6,7-hydroxy groups taken together, methylene or ethylene.

The renal dopaminergic activity of the compounds of this invention was demonstrated by monitoring mean arterial blood pressure (MAP), mean renal blood flow (RBF), renal vascular resistance (RVR) and heart rate (HR) in a normal anesthetized dog in a standard pharmacological procedure. The selected compound is administered by intravenous infusion and is expressed as µg/kg/min. Each dose is infused for five minutes. A clinically useful compound, dopamine, was run as a positive control.

| Compound A: 3-Cyclopropylmethyl-6-chloro-7,8-dihydroxy-1-(p-hydroxyphenyl)-2,3,4,5-tetrahydro-1H-3-benzazepine hydrobromide: | | | | |
|---|---|---|---|---|
| Dose | % Change in 2 Dogs | | | |
| (µg/kg/min) | MAP | RBF | RVR | HR |
| Dopamine 3 | −6.9 | +28.6 | −27.2 | +10.7 |
| A 3 | −3.1 | −2.0 | −0.5 | +0.1 |
| 30 | −0.7 | +14.1 | −12.6 | 0 |
| 300 | −11.5 | +18.2 | −25.8 | −3.2 |

The desired vasodilator activity accompanied by increase in renal blood flow was observed at doses of 30 and 300 µg/kg/min.

The pharmacodynamic methods of this invention comprise administration of an active nontoxic quantity of a compound of Formula I, one of its pharmaceutically acceptable acid addition salts or one of its O-lower alkanoyl esters internally, preferably either orally or parenterally, to a human or animal patient in need or renal vasodilation. The primary desired effect on the kidney is to decrease vascular resistance and increase blood flow. The effect is similar to the renal effects of dopamine and like clinical effects may be thereby realized such as in treating hypertension or other abnormal cardiovascular conditions. The route of administration may be any that effectively transports the active ingredient to the renal receptors but oral, rectal, intravenous or subcutaneous routes of administration are conveniently used. The compound of Formula I is administered in a nontoxic quantity sufficient to induce renal vasodilatation. Most conveniently the active ingredient is combined with a pharmaceutical carrier and administered to the patient from 1-5 times daily as necessary to effect the desired pharmacodynamic result. The daily dosage is based on total quantities of the base of from about 200 mg to about 1 g per day, administered preferably as 100-500 mg of base per dosage unit which is administered from 1-5 times daily orally. The parenteral dosage regimen would be lower than the oral regimen. The daily dosage regimen is selected with the conditions known to be factors in the art, for example, the age and weight of the subject, the severity of the clinical disorder, the route of administration and the relative potency of the active ingredient compared to the activity of dopamine in the test systems described hereafter. When the method of this invention is carried out renal vasodilatation similar to that induced by dopamine is realized.

The pharmaceutical compositions of this invention having renal dilating activity which are of use for treating hypotensive patients are prepared in conventional dosage unit forms by incorporating a compound of Formula I, or a pharmaceutically acceptable acid addition salt or ester derivative thereof, with a nontoxic pharmaceutical carrier according to accepted procedures in a nontoxic amount sufficient to produce the desired pharmacodynamic activity in a subject, animal or human. Preferably, the compositions will contain the active ingredient in an active but nontoxic amount selected from about 100 mg to about 500 mg preferably about 125-350 mg of active ingredient calculated as the base per dosage unit.

The pharmaceutical carrier employed may be, for example, either a solid or liquid. Exemplary of solid carriers are lactose, terra alba, sucrose, talc, gelatin, agar, pectin, acacia, magnesium stearate, stearic acid, and the like. Exemplary of liquid carriers are isotonic saline for parenteral use or syrup, peanut oil, olive oil, water and the like for soft gelatin capsules. Similarly, the carrier or diluent may include any time delay material well known to the art, such as glyceryl monostearate or glyceryl distearate alone or with a wax. Such sustained release products as well as derivatives which may be gradually metabolized to the active parent can be employed to prolong the biological activity of the compounds of this invention.

A wide variety of pharmaceutical forms can be employed ranging from rectal suppositories to sterile solutions for parenteral or injectable use. Thus, if a solid carrier for oral administration is used the preparation can be tableted, placed in a hard gelatin capsule in powder, regular or sustained release pellet or tablet form, or in the form of a troche or lozenge. The amount of solid carrier will vary widely but preferably will be from about 25 mg to about 1 g. If a liquid carrier is used, the preparation will be in the form of a syrup, emulsion, soft gelatin capsule, sterile injectable liquid such as an ampul or an aqueous or nonaqueous liquid suspension.

The pharmaceutical preparations are made following the conventional techniques of the pharmaceutical chemist involving mixing, granulating and compressing when necessary, or variously mixing and dissolving the ingredients as appropriate to give the desired end product.

The following examples are designed to teach the practice of the invention but not to limit its scope. All temperatures are Centigrade.

EXAMPLE 1

A mixture of 2.0 g (0.0058 m) of 6-chloro-7,8-dimethoxy-1-(p-methoxyphenyl)-2,3,4,5-tetrahydro-1H-3-benzazepine, 15 g (0.11 m) of cyclopropanecarboxylic acid and 25 ml of tetrahydrofuran was stirred under nitrogen at 50°-55° while 1.0 g (0.027 m) of sodium borohydride was added over a 30 minute period. Reaction was continued for 4 hours under a nitrogen atmosphere. The reaction mixture was cooled and diluted with 50 ml of cold water. The aqueous mixture was made strongly basic with sodium hydroxide then extracted with methylene chloride. The extract was washed twice with brine, water and then brine again. Evaporation of the dried organic extract gave 2.4 g of yellow oil. Thin layer chromatography showed a mixture present.

The yellow oil in chloroform was passed over a silica gel column and eluted using 2% methanol-chloroform to give 2.1 g of the desired base. The base was converted with hydrogen chloride-methanol to 1.58 g (69%) of the hydrochloride salt of 3-cyclopropylmethyl-6-chloro-7,8-dimethoxy-1-(p-methoxy-phenyl)-2,3,4,5-tetrahydro-1H-3-benzazepine, m.p. 146°-149°.

The trimethoxyhydrochloride (0.98 g, 0.0022 m) in 25 ml of methylene chloride was cooled to −15° then reacted with a mixture of 1.2 ml (0.013 m) of boron tribromide and 10 ml of methylene chloride. After stirring at −15° for one half hour and at room temperature for 2 hours, the mixture was cooled and quenched several times with methanol, the last time with a few drops of 48% hydrogen bromide. Evaporation gave a foam which was crystallized from ethyl acetate-methanol to give 0.87 g (90%) of white solid 3-cyclopropylmethyl-6-chloro-7,8-dihydroxy-1-(p-hydroxyphenyl)-2,3,4,5-tetrahydro-1H-3-benzazepine hydrobromide, m.p. 215°-218°.

Anal. Calcd. for $C_{20}H_{22}ClNO_3 \cdot HBr$: C, 54.50; H, 5.26; N, 3.18. Found: C, 54.48; H, 5.10; N, 3.04.

This compound (150 mg) is mixed with 150 mg of lactose and 2 mg of magnesium stearate then filled into hard gelatin capsule which is administered orally to a hypertensive patient 5 times daily.

Another portion of 500 mg of the hydrobromide salt is shaken with a mixture of ether-5% sodium carbonate solution. The ether layer is divided into three aliquots. Reaction with methane sulfonic acid in ethanol, sulfuric acid in ether or evaporation gives the methane sulfonic acid salt, sulfate or base forms respectively.

EXAMPLE 2

A mixture of 2.0 g of 6-fluoro-7,8-dimethoxy-1-(p-methoxyphenyl)-2,3,4,5-tetrahydro-1H-3-benzazepine hydrochloride, 2.8 g of triethylamine and 25 ml of dimethylformamide is stirred at room temperature then cooled to 0° while 2 g of cyclobutane carboxylic acid chloride is added dropwise. After stirring at room temperature for 2 hours, the mixture is poured into water and the desired 3-cyclobutylcarbonyl intermediate isolated by ethyl acetate extraction.

This material (1 g) in tetrahydrofuran is added dropwise to a suspension of 2.5 g of lithium aluminum hydride in tetrahydrofuran. After stirring the reaction mixture at room temperature overnight, ethyl acetate is added followed by an aqueous solution of ammonium tartrate. The organic layer is separated, evaporated and the residue purified by chloroform extraction and formation of the hydrochloride salt, 3-cyclobutylmethyl-6-fluoro-7,8-dimethoxy-1-(p-methoxyphenyl)-2,3,4,5-tetrahydro-1H-3-benzazepine hydrochloride.

This material (0.8 g) in 20 ml of methylene chloride is reacted with boron tribromide (2.0 ml) in 20 ml of methylene chloride at −15°. After methanol quenching, evaporation gives 3-cyclobutylmethyl-6-fluoro-7,8-dihydroxy-1-(p-hydroxyphenyl)-2,3,4,5-tetrahydro-1H-3-benzazepine as the hydrobromide.

EXAMPLE 3

The procedure of Example 2 is repeated with 6-iodo-7,8-dimethoxy-1-(p-methoxyphenyl)-2,3,4,5-tetrahydro-1H-3-benzazepine and cyclopentanecarboxylic acid chloride as starting materials to give the N-cyclopentylcarbonyl compound then 3-cyclopentylmethyl-6-iodo-7,8-dimethoxy-1-(p-methoxyphenyl)-2,3,4,5-tetrahydro-1H-3-benzazepine hydrobromide, and finally 3-cyclopentylmethyl-6-iodo-7,8-dihydroxy-1-(p-hydroxyphenyl)-2,3,4,5-tetrahydro-1H-3-benzazepine hydrobromide.

EXAMPLE 4

6-Bromo-7,8-dimethoxy-1-(p-methoxyphenyl)-2,3,4,5-tetrahydro-1H-3-benzazepine hydrobromide (3 g) is reacted with cyclohexylcarboxylic acid in the presence of sodium borohydride as in Example 1 to give 6-bromo-3-cyclohexylmethyl-7,8-dimethoxy-1-(p-methoxyphenyl)-2,3,4,5-tetrahydro-1H-3-benzazepine base and, after treatment with boron tribromide, 6-bromo-3-cyclohexylmethyl-7,8-dihydroxy-1-(p-hydroxyphenyl)-2,3,4,5-tetrahydro-1H-3-benzazepine hydrobromide.

EXAMPLE 5

A mixture of 1 g of 3-cyclopropylmethyl-6-chloro-7,8-dihydroxy-1-(p-hydroxyphenyl)-2,3,4,5-tetrahydro-1H-3-benzazepine hydrobromide, 1.3 ml of acetyl bromide and 200 ml of trifluoroacetic acid is heated at reflux for 2 hours. After evaporation to dryness, the residue is purified, if necessary, by recrystallization to give 3-cyclopropylmethyl-6-chloro-7,8-diacetoxy-1-(p-acetoxyphenyl)-2,3,4,5-tetrahydro-1H-3-benzazepine hydrobromide. Similarly tri-isobutyryloxy, -propionyloxy, -isovaleryloxy, -n-butyryloxy and -n-heptanoyloxy ester derivatives are prepared.

What is claimed is:

1. A compound of the structure

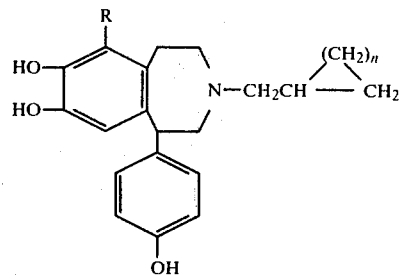

in which R is halo and n is 1, one of its tri-O-lower alkanoyl esters or one of its pharmaceutically acceptable acid addition salts.

2. The compound of claim 1 being 6-chloro-3-cyclopropylmethyl-7,8-dihydroxy-1-(p-hydroxyphenyl)-2,3,4,5-tetrahydro-1H-3-benzazepine.

3. The compound of claim 1 being 6-chloro-3-cyclocyclopropylmethyl-7,8-dihydroxy-1-(p-hydroxyphenyl)-2,3,4,5-tetrahydro-1H-3-benzazepine in the form of a pharmaceutically acceptable acid addition salt.

4. The compound of claim 1 being 6-chloro-3-cyclopropylmethyl-7,8-dihydroxy-1-(p-hydroxyphenyl)-2,3,4,5-tetrahydro-1H-3-benzazepine methane sulfonic acid salt.

* * * * *